US006627412B1

(12) United States Patent
Manning et al.

(10) Patent No.: US 6,627,412 B1
(45) Date of Patent: Sep. 30, 2003

(54) METHOD FOR DETECTING MICROORGANISMS

(75) Inventors: Janet Elizabeth Manning, Goostrey (GB); John Charles Plant, Stone (GB)

(73) Assignee: Osmetech plc (GB)

( * ) Notice: Subject to any disclaimer, the term of this patent is extended or adjusted under 35 U.S.C. 154(b) by 0 days.

(21) Appl. No.: 09/762,369

(22) PCT Filed: Aug. 20, 1999

(86) PCT No.: PCT/GB99/02730

§ 371 (c)(1),
(2), (4) Date: Feb. 1, 2001

(87) PCT Pub. No.: WO00/11209

PCT Pub. Date: Mar. 2, 2000

(30) Foreign Application Priority Data

Aug. 21, 1998 (GB) .............................................. 9818176

(51) Int. Cl.[7] .................................................. C12Q 1/04
(52) U.S. Cl. ................................ 435/29; 435/4; 435/34
(58) Field of Search .................................. 435/29, 34, 4

(56) References Cited

U.S. PATENT DOCUMENTS

| 4,182,656 A | * | 1/1980 | Ahnell et al. | |
| 5,518,895 A | * | 5/1996 | Thorpe et al. | ................ 435/34 |
| 5,858,769 A | * | 1/1999 | DiGuiseppi et al. | ..... 435/287.3 |

FOREIGN PATENT DOCUMENTS

| EP | 0 640 826 A1 | 3/1995 |
| WO | WO 98/29563 | 7/1998 |

OTHER PUBLICATIONS

WO 95/33848. Payne et al. (1995). Detecting bacteria.*

* cited by examiner

Primary Examiner—Leon B. Lankford, Jr.
Assistant Examiner—R. A. Davis
(74) Attorney, Agent, or Firm—Marger Johnson & McCollom, PC

(57) ABSTRACT

There is disclosed a method for detecting microorganisms comprising the steps of: providing a plurality of cultures by culturing said microorganisms on a plurality of different media; making measurements of the cultures; collating the measurements of the cultures; and correlating the collated measurements with the presence of the microorganisms.

18 Claims, 1 Drawing Sheet

METHOD FOR DETECTING MICROORGANISMS

This invention relates to a method for detecting microorganisms.

It is known from International Publication WO95/33848 that microorganisms such as bacteria can be detected by analysing gases emitted by the microorganisms. International Publication WO 98/29563 describes improvements to the method in which variations in the emitted gases caused by variations in culturing conditions are taken account of by providing an enlarged reference database which incorporates reference measurements taken under a variety of culturing conditions. However, both of these documents are primarily concerned with the detection of microorganisms from a single measurement made on a single culture, be it a plate culture or an in vivo measurement on a patient.

The present invention provides an alternative method for detecting microorganisms in which microorganism are cultured on a plurality of culturing media and measurements are made of each culture. In a primary, but non-limiting, embodiment, measurements are made of gaseous atmospheres associated with each culture. The method has been demonstrated to differentiate between different strains of a common microorganism species, and can provide multivariate data using fewer sensors than required in the methods of WO95/133849 and WO98/29563.

For the avoidance of doubt, the term "gaseous" is understood to encompass all species present in the gas phase, including volatile species.

According to the invention there is provided a method for detecting microorganisms comprising the steps of:
 providing a plurality of cultures by culturing said microorganisms on a plurality of different media;
 making measurements of the cultures;
 collating the measurements of the cultures; and
 correlating the collated measurements with the presence of the microorganisms.

Gaseous measurements of the cultures may be made by detecting gaseous species present in gaseous atmospheres associated with each of the cultures using one or more gas sensors.

The method may identify the genus of the microorganisms. Additionally, the species of the microorganisms may be detected. Additionally still, the strain of the microorganisms may be detected.

The microorganisms may comprise bacteria, viruses, microfungi, algae, yeasts, mammalian cells and/or plant cells.

The step of collating the measurements may comprise assigning a descriptor to describe a plurality of measurements.

The step of collating the measurements may comprise obtaining ratios of sensor responses. Responses obtained by measuring different cultures may be ratioed. Alternatively, or additionally, responses obtained from different sensors may be ratioed.

The gas sensor or sensors may comprise a gas sensitive material. Gaseous species may be detected by detecting an electrical, piezoelectrical or optical property of the gas sensitive material.

The gas sensitive material may comprise conducting polymer.

A mass spectrometer may be used to detect gaseous species.

Methods in accordance with the invention will now be described with reference to the accompanying drawings, in which.

In an important embodiment, the invention comprises a method for detecting microorganisms comprising the steps of:
 providing a plurality of cultures by culturing said microorganisms on a plurality of different media;
 making gaseous measurements of the cultures by detecting gaseous species present in gaseous atmospheres associated with each of the cultures using one or more gas sensors;
 collating the gaseous measurements of the cultures; and
 correlating the collated measurements with the presence of the microorganisms.

Figure 1:
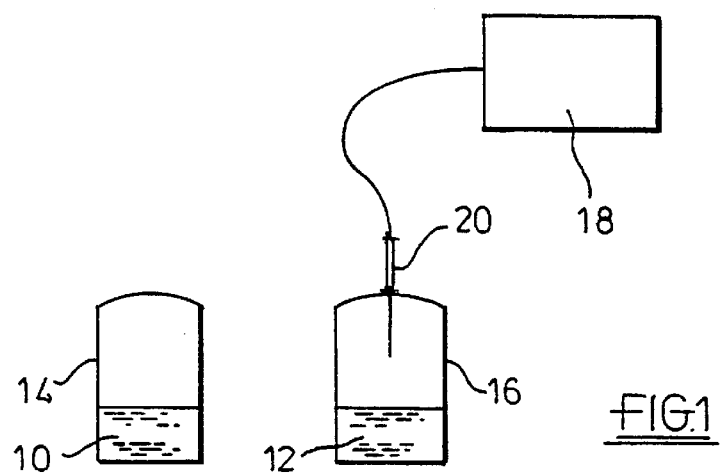
FIG. 1 shows apparatus for making gaseous measurements.

FIG. 1 depicts the making of the gaseous measurements on two cultures 10, 12 of the same microorganism contained within containers 14, 16. It will be appreciated that the use of more cultures is within the scope of the invention and, indeed, will probably be desirable in many instances. The headspaces above the cultures comprise gaseous atmospheres which are sampled by a gas sensor 18 in a suitable manner. In the example depicted in the Figure, gaseous atmospheres are sampled using a syringe 20 and pumped across the gas sensor using suitable pumping means (not shown).

It is known from WO94/33848 that the gaseous atmospheres associated with the microorganism cultures are characteristic of the microorganisms due to the presence of certain gaseous species which are produced, for example, by microorganism metabolism. It is known from WO 98/29563 that the composition of the gaseous atmosphere varies depending on the culturing medium used. Neither of these documents teach or even suggest that these culture dependent variations can turned to advantage by making measurements using a plurality of media. The present invention recognises that the differences between the gaseous atmospheres associated with different media can be indicative of the microorganism concerned. By using a plurality of media, multivariate data is produced, even with a single, non-specific gas sensor. Thus, the plurality of different media takes the place, either partially or wholly, of an array of sensors.

EXAMPLE 1

Experiments were performed using two media: a standard broth (broth 1) and a standard broth with an antibiotic (broth 2). Both experiments were performed at room temperature. In one experiment, cultures of the bacterium *Staphylococcus aureus* were prepared using the two broths. In a second experiment. cultures of the bacterium methicillin resistant *Staphylococcus aureus* (MRSA) were prepared using the two broths. MRSA is an antibiotic resistant strain of *S. aureus*. Two conducting polymer gas sensors (herein after denoted A and B) were used to sample the gaseous atmospheres associated with the different cultures. The two conducting polymer gas sensors are components of a thirty two sensor array manufactured by the applicants. It should be noted that a characteristic of such conducting polymer sensors is that a given conducting polymer is usually responsive to a number of different gases. Thus, the sensors A and B are non-specific in nature. Furthermore, the response of these sensors is represented by a single value, namely the variation in the dc resistance of the sensor. Thus it is not generally possible to ascertain from this single response the identity of the gas species which are responsible for producing it. However, as will become apparent, it is not necessary that their identities are known.

Table 1 shows the response of sensor A after gaseous measurements of the different broth/bacteria combinations. Table 2 shows the corresponding responses obtained with sensor B. It can be seen that MRSA produces gas sensor responses which are reasonably insensitive to the culturing medium employed. In contrast, gas sensor responses associated with *S. aureus* are considerably reduced when broth 2 is used as a culturing medium. Thus, it is possible to distinguish between *S. aureus* and MRSA using different culturing media. Furthermore, only a single conducting polymer sensor is required. This is in contrast to WO 95/33848 and WO 98/29563, which require the use of entire arrays of conducting polymer sensors when the sensors are interrogated by measuring dc resistance. (It is possible to utilise other interrogating techniques, such as ac interrogation).

There are a number of ways in which the gaseous measurements might be collated in order to determine information about the microorganism. For example, it is possible to assign a descriptor to describe a plurality of measurements. This might consist of a string which represents the responses of the gas sensor obtained using different media. In the present example, a descriptor for *S. aureus* using sensor A could be 110216, this string being (response with broth 2×10 & response with broth 1×10). With sensor B, the descriptor for *S. aureus* would be 049120. For MRSA, the associated descriptors are 218238 and 109137 for sensors A and B, respectively. Another approach would be to define bands of sensor response, perhaps assigning a letter to each. For example, a sensor response between 0 and 1 might be assigned the letter 'A', a response between 1 and 2 might be 'B', etc. This approach would allow some leeway for random experimental variations in the gaseous measurements.

Another way of collating data is one in which ratios of sensor responses are obtained. The responses obtained by measuring different cultures might be ratioed. In the present example the ratios might comprise the ratio of response to broth 1 to response to broth 2. Thus, *S. aureus* would be described by a ratio of 1.96 with sensor A and by a ratio of 2.45 with sensor B. MRSA would be described by ratios of 1.09 and 1.26 with sensors A and B respectively. The advantage of such an approach is that sensor gain is compensated for, so that, for example, the results obtained using sensor A could be compared with results obtained using another sensor of the same type which might, due to factors such as variations in manufacturing conditions, exhibit a different sensitivity. The approach will also compensate for variations in microorganism concentration between different experiments caused by variations in factors such as the initial number of microorganisms present, provided the ratio of the numbers of microorganisms initially present on different media is constant between experiments. It will be apparent that if more culturing media are used, more complex ratios will result. The responses might be ratioed to the response obtained with a choosen medium, or some form of normalisation might be employed. For the avoidance of doubt, a normalisation procedure is taken to be an example of ratioing for the present purposes.

Alternatively, or additionally, reponses obtained from different sensors might be ratioed. The advantage of doing this is that concentration effects are accounted for, at least in the linear response regime of the sensors, even in the instance in which different media are innoculated with different numbers of microorganisms.

In the above example, the substantial decrease in sensor response observed when *S. aureus* is cultured on broth 2 is undoubtedly due in large measure to the fact that the population of *S. aureus* is diminished by the antibiotic. However, it is also possible that the composition of the gaseous atmosphere is different. In other instances, it is possible that differences between measurements made on different cultures will be primarily due to differences in the nature of the associated gaseous atmosphere.

EXAMPLE 2

Experiments were performed on two cultures of *Enterococcus faecalis*. In one instance, *E. faecalis* was cultured in broth, whereas in the other instance the amino acid arginine was added to the broth, and *E. faecalis* was cultured therein. A thirty two sensor conducting polymer gas sensor array (manufactured by the applicants) was used to sample the gaseous atmospheres associated with the cultures, measurements being made by observing the change in the dc resistance of the sensor.

Figure 2:
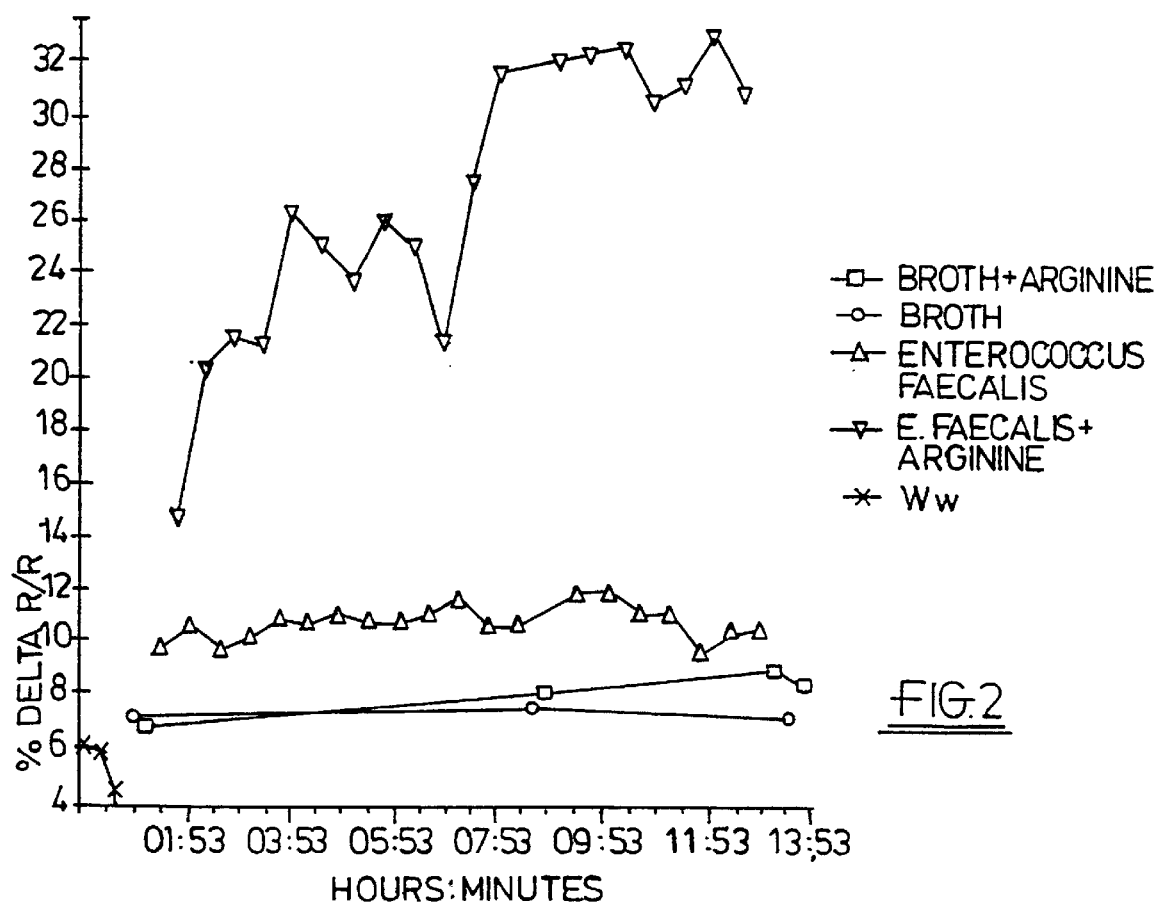
FIG. 2 shows the response of a gas sensor to headspaces above cultures of *Enterococcus faecalis*.

FIG. 2 shows the average response of the gas sensors in the array to the gaseous atmospheres above the two cultures, together with the responses associated with various control experiments. Data marked Δ correspond to measurements made on the broth+*E. faecalis* culture, and data marked ▼ correspond to measurements made on the broth+arginine+*E. faecalis* culture. Data marked ■ correspond to a broth and arginine control, data marked ● correspond to a broth only control, and data marked 1 relates to a water sample.

FIG. 2 clearly shows a marked increase in signal when anginine is added to the broth/*E. faecalis* culture. Almost certainly, this is due to amonia being released as a breakdown product following hydrolysis of arginine by *E. faecalis*. The conducting polymer gas sensors are sensititve inter alia to ammonia.

If a measurement is performed on the broth+*E. faecalis* culture alone, very little information is obtained. In fact, the detected signal is barely distinguishable from the control experiments. By providing an extra measurement using a broth containing arginine, extra information is obtained. Thus, if an unknown microorganism produced results similar to those shown in FIG. 2, the identity of the microorganism could be reasonably narrowed to the subset of species which provide no significant gaseous signature in broth, but which are capable of hydrolysing arginine. The use of more gas sensors and/or further culturing media could provide an even more precise identification.

Note that a measurement as performed on the broth+arginine+*E. faecalis* culture alone would not provide a great deal of information, since it would not be possible to know whether the relatively large observed signal is due to evolved ammonia or some other metabolic product or, indeed, a combination of species.

Other forms of gas sensor might be employed, including other forms of gas sensors which comprise a gas sensitive material, such as metal oxide, SAW, and quartz crystal sensors. Another possibility is electrochemical cells. It might be possible to detect a single gaseous species, such as carbon dioxide or ammonia. Analytical instruments such as GC, GC-MS, mass spectrometers, and spectroscopic techniques, such as FTIR, might be employed. It will be appreciated by the skilled reader that such instruments do not merely provide a single response output which has contributions from an unknown number of gas species. Rather, the presence of different gaseous species can, at least in principle, be deduced, for example from a mass spectrometric cracking pattern or firm characteristic peaks in an infra-red spectrum. It is possible that, since the present invention provides additional information by providing a plurality of measurements on different cultures of the same microorganism, it would not be necessary to utilise or analyse all of the information obtainable with a given technique. For example, it might prove possible to monitor a small number of m/z peak corresponding to certain characteristic gaseous species, using a mass spectrometer.

The following are examples of substances which might be added, either individually or in combination, to a medium in order to produce further distinct culturing media: carbohydrates, such as hexoses (e.g. glucose, lactose, galactose) and disaccharides (e.g. melibose, trehalose); alcohols, such as manntol and sorbitol; amino acids, such as arginine, lysine and ornithine; and organic acids such as citric acid.

Although, as described above, the use of gaseous measurements is of primary interest to the applicants, the invention is not limited in this way. It is possible to perform other measurements on different cultures of a microorganism and thus to detect the microorganism by examining how these measurements depend on the medium used. There are many forms that these measurements might take. Instead of gas sensors, liquid phase sensors might be employed Changes in pH or glucose uptake might be monitored. Fluorescence or luminescence techniques, such as the monitoring of ATP by luminescence generated with an enzyme such as luciferase, can be used. Another possibility is to employ a technique which monitors protein changes. It may be possible to derive useful information from simple cell counts.

In practice, the steps of collating the measurements and correlating these measurements with the presence of the microorganisms would be performed using a suitable adapted computer. Possible ways of performing the correlation include chemometric techniques, comparisons with reference measurements and neural network techniques.

TABLE 1

Responses using Sensor A

|         | MRSA | S. aureus |
|---------|------|-----------|
| Broth 1 | 23.8 | 21.6      |
| Broth 2 | 21.8 | 11.0      |

TABLE 2

Responses using Sensor B

|         | MRSA | S. aureus |
|---------|------|-----------|
| Broth 1 | 13.7 | 12.0      |
| Broth 2 | 10.9 | 4.9       |

What is claimed is:

1. A method for identifying a microorganism, comprising:
   providing a plurality of cultures grown in a plurality of varying culture media, said plurality of cultures having a corresponding plurality of gaseous atmospheric headspaces thereover;
   exposing one or more chemically-responsive gas sensors to the plurality of gaseous headspaces;
   generating a plurality of sensor response signals, each of said response signals being proportionate to a concentration of a gaseous species present in the gaseous headspace;
   collating the plurality of sensor response signals; and
   correlating the collated sensor response signals with the presence of a specific microorganism.

2. A method according to claim 1 for identifying the genus of the microorganisms.

3. A method according to claim 2 for identifying the species of the microorganisms.

4. A method according to claim 3 for identifying the strain of the microorganisms.

5. A method according to any of claims 1, 2, 3 and 4 in which the microorganism comprises a bacterium.

6. A method according to any of claims 1, 2, 3 and 4 in which the microorganism comprises a virus, microfungusi, alga, yeast, mammalian cells and/or plant cell.

7. A method according to any of claims 1, 2, 3 and 4 in which the step of collating the plurality of sensor response signals comprises assigning a descriptor to describe a plurality of plurality of sensor response signals.

8. A method according to any of claims 1, 2, 3 and 4 in which the step of collating the plurality of sensor response signals comprises obtaining ratios of sensor response signals.

9. A method according to claim 8 in which responses signals obtained by measuring different cultures are ratioed.

10. A method according to claim 8 in which responses signals obtained from different sensors are ratioed.

11. A method according to claim 1 in which the gas sensor or sensors comprise a gas sensitive material.

12. A method according to claim 11 in which gaseous species are detected by detecting an electrical, piezoelectrical or optical property of the gas sensitive material.

13. A method according to claim 12 in which the gas sensitive material comprises conducting polymer.

14. A method according to any of claims 1, 2, 3 and 4 in which a mass spectrometer is used to detect gaseous species.

15. A method for identifying a specific microorganism, comprising:
   providing a plurality of cultures grown in a plurality of varying culture media, said plurality of cultures having a corresponding plurality of gaseous atmospheric headspaces thereover;
   exposing one or more chemically-responsive gas sensors to the plurality of headspaces;
   generating a plurality of sensor response signals, each of said response signals being proportionate to a concentration of a gaseous species present in the gaseous headspace;
   collating the plurality of sensor response signals into a gas sensor response pattern; and
   correlating the gas sensor response pattern with the presence of the microorganism.

16. The method of claim 15 wherein the microorganism comprises a bacterium, virus, microfungus, alga, yeast, mammalian cell and/or plant cell.

17. The method of claim 15 wherein collating the measurements comprises obtaining ratios of sensor response signals.

18. A method according to claim 17 in which response signals are ratioed.

* * * * *

UNITED STATES PATENT AND TRADEMARK OFFICE
CERTIFICATE OF CORRECTION

PATENT NO.    : 6,627,412 B1                                        Page 1 of 1
DATED         : September 30, 2003
INVENTOR(S)   : Manning et al.

It is certified that error appears in the above-identified patent and that said Letters Patent is hereby corrected as shown below:

<u>Title page,</u>
Item [30], Foreign Application Priority Data, "Aug. 21, 1998   (GB)......9818176" should read -- Aug. 21, 1998     (GB).......9818176.1 --.

<u>Column 1,</u>
Line 11, "incorporates reference measurements" should read -- incorporates reference measurements --.
Line 25, "of WO 95/133849" should read -- of WO 95/33848 --.

<u>Column 2,</u>
Line 50, "experiment. Cultures" should read -- experiment, cultures --.

<u>Column 5,</u>
Line 5, "of m/z peak corresponding" should read -- of m/z peaks, corresponding --.

<u>Column 6,</u>
Lines 5, 7, and 9, "the microorganisms." should read -- the microorganism. --.
Line 14, "virus, microfungusi, alga," should read -- virus, microfungus, alga --.
Line 15, "mammalian cells and/or" should read -- mammalian cell and/or --.
Line 24, "which responses signals" should read -- which response signals --.
Line 26, "which responses signals" should read -- which response signals --.

Signed and Sealed this

Fifteenth Day of June, 2004

JON W. DUDAS
*Acting Director of the United States Patent and Trademark Office*